United States Patent
Schrodi

(10) Patent No.: US 9,255,117 B2
(45) Date of Patent: Feb. 9, 2016

(54) SYNTHESIS OF TERMINAL ALKENES FROM INTERNAL ALKENES AND ETHYLENE VIA OLEFIN METATHESIS

(71) Applicant: MATERIA, INC., Pasadena, CA (US)

(72) Inventor: Yann Schrodi, Northridge, CA (US)

(73) Assignee: MATERIA, INC., Pasadena, CA (US)

( * ) Notice: Subject to any disclaimer, the term of this patent is extended or adjusted under 35 U.S.C. 154(b) by 0 days.

(21) Appl. No.: 13/965,845

(22) Filed: Aug. 13, 2013

(65) Prior Publication Data

US 2014/0200382 A1    Jul. 17, 2014

Related U.S. Application Data

(60) Continuation of application No. 13/913,814, filed on Jun. 10, 2013, now Pat. No. 9,139,605, which is a division of application No. 13/234,542, filed on Sep. 16, 2011, now Pat. No. 8,481,747, which is a division of application No. 11/879,029, filed on Jul. 13, 2007, now Pat. No. 8,067,610.

(60) Provisional application No. 60/830,944, filed on Jul. 13, 2006.

(51) Int. Cl.
- *C07F 15/00* (2006.01)
- *B01J 31/22* (2006.01)
- *C07C 6/04* (2006.01)
- *C07C 67/333* (2006.01)

(52) U.S. Cl.
CPC ......... *C07F 15/0046* (2013.01); *B01J 31/2265* (2013.01); *C07C 6/04* (2013.01); *C07C 67/333* (2013.01); *B01J 2231/543* (2013.01); *B01J 2531/821* (2013.01); *C07C 2531/22* (2013.01); *C07C 2531/24* (2013.01)

(58) Field of Classification Search
CPC .................................................. C07F 15/0046
See application file for complete search history.

(56) References Cited

U.S. PATENT DOCUMENTS

| | | | |
|---|---|---|---|
| 2,619,422 A | 11/1952 | Whiting | |
| 3,448,178 A | 6/1969 | Flanagan | |
| 3,896,053 A | 7/1975 | Broecker et al. | |
| 4,634,606 A | 1/1987 | Skogg | |
| 5,043,485 A | 8/1991 | Fleckenstein et al. | |
| 5,142,072 A | 8/1992 | Stipp et al. | |
| 5,312,940 A | 5/1994 | Grubbs et al. | |
| 5,506,363 A | 4/1996 | Grate et al. | |
| 5,639,526 A | 6/1997 | Kotsiopoulos et al. | |
| 5,700,516 A | 12/1997 | Sandvick et al. | |
| 5,710,298 A | 1/1998 | Grubbs et al. | |
| 5,728,785 A | 3/1998 | Grubbs et al. | |
| 5,728,917 A | 3/1998 | Grubbs et al. | |
| 5,734,070 A | 3/1998 | Tacke et al. | |
| 5,750,815 A | 5/1998 | Grubbs et al. | |
| 5,811,515 A | 9/1998 | Grubbs et al. | |
| 5,831,108 A | 11/1998 | Grubbs et al. | |
| 5,849,851 A | 12/1998 | Grubbs et al. | |
| 5,880,231 A | 3/1999 | Grubbs et al. | |
| 5,917,071 A | 6/1999 | Grubbs et al. | |
| 5,922,863 A | 7/1999 | Grubbs et al. | |
| 5,939,504 A | 8/1999 | Woodson, Jr. et al. | |
| 5,969,170 A | 10/1999 | Grubbs et al. | |
| 5,977,393 A | 11/1999 | Grubbs et al. | |
| 6,020,443 A | 2/2000 | Woodson, Jr. et al. | |
| 6,040,363 A | 3/2000 | Warner et al. | |
| 6,063,144 A | 5/2000 | Calzada et al. | |
| 6,080,826 A | 6/2000 | Grubbs et al. | |
| 6,107,420 A | 8/2000 | Grubbs et al. | |

(Continued)

FOREIGN PATENT DOCUMENTS

DE    19956226         5/2001
EP    0429995 A2       6/1991

(Continued)

OTHER PUBLICATIONS

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

(Continued)

*Primary Examiner* — Joseph Kosack

(74) *Attorney, Agent, or Firm* — J.A. Lindeman & Co., PLLC

(57) ABSTRACT

This invention relates generally to olefin metathesis, and more particularly relates to the synthesis of terminal alkenes from internal alkenes using a cross-metathesis reaction catalyzed by a selected olefin metathesis catalyst. In one embodiment of the invention, for example, a method is provided for synthesizing a terminal olefin, the method comprising contacting an olefinic substrate comprised of at least one internal olefin with ethylene, in the presence of a metathesis catalyst, wherein the catalyst is present in an amount that is less than about 1000 ppm relative to the olefinic substrate, and wherein the metathesis catalyst has the structure of formula (II)

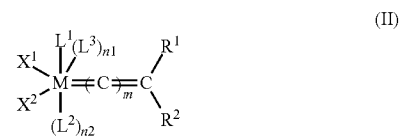

(II)

wherein the various substituents are as defined herein. The invention has utility, for example, in the fields of catalysis, organic synthesis, and industrial chemistry.

9 Claims, 1 Drawing Sheet

(56) References Cited

U.S. PATENT DOCUMENTS

| | | |
|---|---|---|
| 6,169,198 B1 | 1/2001 | Fischer et al. |
| 6,197,894 B1 | 3/2001 | Sunaga et al. |
| 6,211,315 B1 | 4/2001 | Lanrock et al. |
| 6,214,918 B1 | 4/2001 | Johnson et al. |
| 6,215,019 B1 | 4/2001 | Pederson et al. |
| 6,224,641 B1 | 5/2001 | Matzat et al. |
| 6,255,375 B1 | 7/2001 | Michelman |
| 6,262,153 B1 | 7/2001 | Webster et al. |
| 6,281,163 B1 | 8/2001 | Van Dijk |
| 6,284,007 B1 | 9/2001 | Tao |
| 6,284,852 B1 | 9/2001 | Lynn et al. |
| 6,306,988 B1 | 10/2001 | Grubbs et al. |
| 6,310,121 B1 | 10/2001 | Woodson, Jr et al. |
| 6,316,380 B1 | 11/2001 | Nolan et al. |
| 6,323,296 B1 | 11/2001 | Warner et al. |
| 6,376,690 B1 | 4/2002 | Grubbs et al. |
| 6,409,875 B1 | 6/2002 | Giardello et al. |
| 6,410,110 B1 | 6/2002 | Warner et al. |
| 6,410,666 B1 | 6/2002 | Grubbs et al. |
| 6,426,419 B1 | 7/2002 | Grubbs et al. |
| 6,433,101 B1 | 8/2002 | Woodson et al. |
| 6,465,590 B1 | 10/2002 | Maughon et al. |
| 6,486,264 B1 | 11/2002 | Tsunogae et al. |
| 6,503,285 B1 | 1/2003 | Murphy |
| 6,525,125 B1 | 2/2003 | Giardello et al. |
| 6,583,236 B1 | 6/2003 | Giardello et al. |
| 6,586,506 B2 | 7/2003 | Webster et al. |
| 6,599,334 B1 | 7/2003 | Anderson |
| 6,610,626 B2 | 8/2003 | Grubbs et al. |
| 6,613,910 B2 | 9/2003 | Grubbs et al. |
| 6,620,955 B1 | 9/2003 | Pederson et al. |
| 6,645,261 B2 | 11/2003 | Murphy et al. |
| 6,696,597 B2 | 2/2004 | Pederson et al. |
| 6,716,155 B2 | 4/2004 | Sleeter |
| 6,730,137 B2 | 5/2004 | Pesu et al. |
| 6,759,537 B2 | 7/2004 | Grubbs et al. |
| 6,770,104 B2 | 8/2004 | Murphy |
| 6,773,469 B2 | 8/2004 | Murphy |
| 6,794,534 B2 | 9/2004 | Grubbs et al. |
| 6,797,020 B2 | 9/2004 | Murphy |
| 6,803,429 B2 | 10/2004 | Morgan et al. |
| 6,818,586 B2 | 11/2004 | Grubbs et al. |
| 6,824,572 B2 | 11/2004 | Murphy |
| 6,838,489 B2 | 1/2005 | Bell et al. |
| 6,846,573 B2 | 1/2005 | Seydel |
| 6,884,859 B2 | 4/2005 | Grubbs et al. |
| 6,900,347 B2 | 5/2005 | Paulson et al. |
| 6,921,735 B2 | 7/2005 | Hoveyda et al. |
| 6,921,736 B1 | 7/2005 | Nolan et al. |
| 6,946,533 B2 | 9/2005 | Grubbs et al. |
| 6,962,729 B2 | 11/2005 | Tokas et al. |
| 6,987,154 B2 | 1/2006 | Choi et al. |
| 7,026,495 B1 | 4/2006 | Pederson et al. |
| 7,034,096 B2 | 4/2006 | Choi et al. |
| 7,109,348 B1 | 9/2006 | Nolan |
| 7,119,216 B2 | 10/2006 | Newman et al. |
| 7,128,766 B2 | 10/2006 | Murphy et al. |
| 7,176,336 B2 | 2/2007 | Maughon et al. |
| 7,192,457 B2 | 3/2007 | Murphy et al. |
| 7,205,424 B2 | 4/2007 | Nolan |
| 7,217,301 B2 | 5/2007 | Murphy et al. |
| 7,285,593 B1 | 10/2007 | Giardello et al. |
| 7,314,904 B2 | 1/2008 | Nadolsky et al. |
| 7,329,758 B1 | 2/2008 | Grubbs et al. |
| 7,365,140 B2 | 4/2008 | Piers et al. |
| 7,462,205 B2 | 12/2008 | Murphy |
| 7,507,854 B2 | 3/2009 | Lee et al. |
| 7,576,227 B2 | 8/2009 | Lysenko |
| 7,585,990 B2 | 9/2009 | Toor et al. |
| 7,598,330 B2 | 10/2009 | Grubbs et al. |
| 7,622,590 B1 | 11/2009 | Nolan et al. |
| 7,678,932 B2 | 3/2010 | Thurier et al. |
| 7,812,185 B2 | 10/2010 | Burdett et al. |
| 2001/0051680 A1 | 12/2001 | webster et al. |
| 2002/0095007 A1 | 7/2002 | Larock et al. |
| 2002/0157303 A1 | 10/2002 | Murphy et al. |
| 2003/0017431 A1 | 1/2003 | Murphy |
| 2003/0046860 A1 | 3/2003 | Tiffany et al. |
| 2003/0055262 A1 | 3/2003 | Grubbs et al. |
| 2003/0057599 A1 | 3/2003 | Murphy et al. |
| 2003/0061760 A1 | 4/2003 | Tao et al. |
| 2003/0091949 A1 | 5/2003 | Pesu et al. |
| 2003/0100776 A1 | 5/2003 | Grubbs et al. |
| 2003/0110683 A1 | 6/2003 | Murphy |
| 2003/0186035 A1 | 10/2003 | Cruce et al. |
| 2003/0198826 A1 | 10/2003 | Seydel |
| 2003/0207971 A1 | 11/2003 | Stuart, Jr. et al. |
| 2003/0236377 A1 | 12/2003 | Choi et al. |
| 2004/0047886 A1 | 3/2004 | Murphy et al. |
| 2004/0088907 A1 | 5/2004 | Murphy |
| 2004/0088908 A1 | 5/2004 | Murphy |
| 2004/0200136 A1 | 10/2004 | Tao et al. |
| 2004/0221503 A1 | 11/2004 | Murphy et al. |
| 2004/0221504 A1 | 11/2004 | Murphy |
| 2005/0014664 A1 | 1/2005 | Nadolsky et al. |
| 2005/0027136 A1 | 2/2005 | Toor et al. |
| 2005/0060927 A1 | 3/2005 | Murphy |
| 2005/0070750 A1 | 3/2005 | Newman et al. |
| 2005/0080301 A1 | 4/2005 | Maughon et al. |
| 2005/0123780 A1 | 6/2005 | Seydel |
| 2005/0154221 A1 | 7/2005 | Lysenko et al. |
| 2005/0158679 A1 | 7/2005 | Chen et al. |
| 2005/0261451 A1 | 11/2005 | Ung et al. |
| 2005/0269728 A1 | 12/2005 | Roos |
| 2006/0079704 A1 | 4/2006 | Lacombe et al. |
| 2006/0128912 A1 | 6/2006 | Piers et al. |
| 2006/0236593 A1 | 10/2006 | Cap |
| 2006/0272199 A1 | 12/2006 | Licciardello et al. |
| 2006/0272200 A1 | 12/2006 | Murphy et al. |
| 2006/0289138 A1 | 12/2006 | Borsinger et al. |
| 2007/0006522 A1 | 1/2007 | Tao |
| 2007/0039237 A1 | 2/2007 | Murphy et al. |
| 2007/0144058 A1 | 6/2007 | Chen et al. |
| 2007/0151480 A1 | 7/2007 | Bloom et al. |
| 2007/0179307 A1 | 8/2007 | Olivier-Bourbigou et al. |
| 2007/0270621 A1 | 11/2007 | Millis et al. |
| 2007/0282000 A1 | 12/2007 | Murphy et al. |
| 2008/0027194 A1 | 1/2008 | Schrodi |
| 2008/0064891 A1 | 3/2008 | Lee |
| 2009/0048459 A1 | 2/2009 | Tupy et al. |
| 2009/0126602 A1 | 5/2009 | Murphy et al. |
| 2009/0217568 A1 | 9/2009 | Murphy et al. |
| 2009/0220443 A1 | 9/2009 | Braksmayer et al. |
| 2009/0259065 A1 | 10/2009 | Abraham et al. |
| 2009/0264672 A1 | 10/2009 | Abraham et al. |
| 2010/0047499 A1 | 2/2010 | Braksmayer et al. |
| 2010/0094034 A1 | 4/2010 | Kaido et al. |
| 2010/0145086 A1 | 6/2010 | Schrodi et al. |

FOREIGN PATENT DOCUMENTS

| | | |
|---|---|---|
| EP | 1408064 A1 | 4/2004 |
| EP | 1810960 A1 | 7/2007 |
| FR | 2878246 A1 | 5/2006 |
| JP | 56-077243 A | 6/1981 |
| JP | 09-014574 A | 1/1997 |
| RU | 1565872 A1 | 5/1990 |
| WO | 94/23836 A1 | 10/1994 |
| WO | 96/04289 A1 | 2/1996 |
| WO | 00/46565 A1 | 8/2000 |
| WO | 01/36368 A2 | 5/2001 |
| WO | 03/018905 A1 | 3/2003 |
| WO | 03/057983 A1 | 7/2003 |
| WO | 03/093215 A1 | 11/2003 |
| WO | 03/104348 A1 | 12/2003 |
| WO | 2004/033388 A1 | 4/2004 |
| WO | 2004/062763 A2 | 7/2004 |
| WO | 2004/083310 A1 | 9/2004 |
| WO | 2005/026106 A1 | 3/2005 |
| WO | 2005/042655 A2 | 5/2005 |
| WO | 2005/080455 A1 | 9/2005 |
| WO | 2006/052688 A2 | 5/2006 |
| WO | 2006/076364 A2 | 7/2006 |
| WO | 2007/002999 A1 | 1/2007 |

(56) References Cited

FOREIGN PATENT DOCUMENTS

| WO | 2007/081987 A2 | 7/2007 |
|---|---|---|
| WO | 2007/103398 A1 | 9/2007 |
| WO | 2007/103460 A2 | 9/2007 |
| WO | 2008/008420 A1 | 1/2008 |
| WO | 2008/010961 A2 | 1/2008 |
| WO | 2008/046106 A2 | 4/2008 |
| WO | 2008/048520 A2 | 4/2008 |
| WO | 2008/048522 A1 | 4/2008 |
| WO | 2008/063322 A2 | 5/2008 |
| WO | 2008/140468 A2 | 11/2008 |

OTHER PUBLICATIONS

Baumann et al., "Natural Fats and Oils—Renewable Raw Materials for the Chemical Industry," Angewandte Chemie International Edition in English, vol. 27, 1988, pp. 41-62.
Biermann et al., "New Synthesis with Oils and Fats as Renewable Raw Materials for the Chemical Industry," Angewadte Chemie International, vol. 39, 2000, pp. 2206-2224.
Boelhouwer et al., "Metathesis Reactions of Fatty Acid Esters," Progress of Lipid Research, Pergamon Press, vol. 24, No. 3, 1985, pp. 243-267.
Chatterjee et al., "Synthesis of Trisubstituted Alkenes via Olefin Cross-Metathesis," Organic Letters, vol. 1, No. 11, 1999, pp. 1751-1753.
Choi et al., "Olefin Metathesis Involving Ruthenium Enoic Carbene Complexes," Journal of the American Chemical Society, vol. 123, No. 42, 2001, pp. 10417-10418.
Connon et al., "A Solid-Supported Phosphine-Free Ruthenium Alklyidene for Olefin Metathesis in Methanol and Water," Bioorganic & Medical Chem Letters, vol. 12, No. 14, 2002, pp. 1873-1876.
Delaude et al., "Metathesis," Kirk-Othmer Encyclopedia of Chemical Technology, Dec. 2005, vol. 26, pp. 920-958.
Dunne et al., "A Highly Efficient Olefin Metathesis Initiator: Improved Synthesis and Reactivity Studies," Tetrahedron Letters, vol. 44, No. 13, 2003, pp. 2733-2736.
Erhan et al., "Drying Properties of Metathesized Soybean Oil," Journal of American Oil Chemists' Society, AOCS Press, vol. 74, No. 6, 1997, pp. 703-706.
Feuge et al., "1,3-Diolein and 1,3-Distearin Esters of Fumaric, Succinic and Adipic Acids," Journal of American Chemical Society, vol. 80, 1958, pp. 6338-6341.
Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.
Maynard et al., "Purification Technique for the Removal of Ruthenium from Olefin Metathesis Reaction Products," Tetrahedron Letters, vol. 40, No. 22, 1999, pp. 4137-4140.
Mol, "Applications of Olefin Metathesis in Oleochemistry: An Example of Green Chemistry," Green Chemistry, Royal Society of Chemistry, Cambridge, GB, vol. 4, 2002, pp. 5-13.
Mol et al., "Metathesis in Oleochemistry," J Braz Chem Soc, vol. 9, No. 1, 1998, pp. 1-11.
Mol, "Catalytic Metathesis of Unsaturated Fatty Acid Esters and Oils," Topics in Catalysis, vol. 27, No. 1-4, 2004, pp. 97-104.
Ngo et al., "Metathesis of Unsaturated Fatty Acids: Synthesis of Long-Chain Unsaturated-[alpha],[omega]-Diacarboxylic Acids," Journal of the American Oil Chemists, Jul. 2006, vol. 83m, Iss 7, p. 629, 9 pgs.
Patel et al., "High Conversion and Productive Catalyst Turnovers in Cross-Metathesis Reactions of NAtural Pils with 2-Butene," Green Chemistry, 2006, vol. 8, pp. 450-454.
Refvik et al., "Ruthenium-Catalyzed Metathesis of Vegetable Oils," Journal of American Oil Chemists' Society, JAOCS Press, vol. 76, No. 1, 1999, pp. 93-98.
Refvik, M.D. et al., "The Chemistry of Metathesized Soybean Oil," JAOCS, vol. 76, No. 1, 1999, pp. 99-102.
Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.
Shorland, "Glycol Esters of Dibasic Acides. The Di-B-hydroxyethyl Esters," Journal of American Chemical Society, vol. 57, No. 1, 1935, pp. 115-116.
Tian et al., "Model Studies and the ADMET Polymerization of Soybean Oil," Journal of American Oil Chemists' Society, AOCS Press, vol. 79, No. 5, 2002, pp. 479-488.
Ward et al., "New Fat Products: Glyceride Esters of Adipic Acid," Journal of the American Oil Chemists' Society, vol. 36, 1959, pp. 667-671.
International Search Report for International Application No. PCT/US2007/016010, dated Mar. 11, 2008, 4 pages.
Courchay et al., "Metathesis Activity and Stability of New Generation Ruthenium Polymerization Catalysts," Macromolecules, vol. 36, 2003, pp. 8231-8239.
International Search Report and Written Opinion of the International Searching Authority for International Application No. PCT/US2006/000822, dated Jul. 14, 2006, 13 pages.
International Search Report for International Application No. PCT/US2007/015905, dated Apr. 23, 2008, 3 pages.
International Search Report and Written Opinion of the International Searching Authority for International Application No. PCT/US2007/00610, dated Oct. 11, 2007, 8 pages.
International Search Report and Written Opinion of the International Searching Authority for International Application No. PCT/US2007/005736, dated Aug. 8, 2007, 11 pages.
International Search Report and Written Opinion of the International Searching Authority for International Application No. PCT/US2007/005868, dated Nov. 9, 2007, 7 pages.
International Search Report for International Application No. PCT/US2007/015866, dated Nov. 26, 2007, 3 pages.
International Search Report for International Application No. PCT/US2007/021931, dated Apr. 11, 2008, 3 pages.
International Search Report for International Application No. PCT/US2007/021934, dated Jun. 17, 2008, 3 pages.
International Search Report for International Application No. PCT/US2007/021939, dated Feb. 18, 2008, 2 pages.
International Search Report and Written Opinion of the International Searching Authority for International Application No. PCT/US2008/009604, dated Oct. 27, 2008, 6 pages.
International Search Report and Written Opinion of the International Searching Authority for International Application No. PCT/US2008/009635, dated Oct. 27, 2008, 7 pages.
International Search Report for International Application No. PCT/US2008/065395, dated Sep. 29, 2008, 1 page.
International Search Report for International Application No. PCT/US2008/067025, dated Sep. 8, 2008, 1 page.

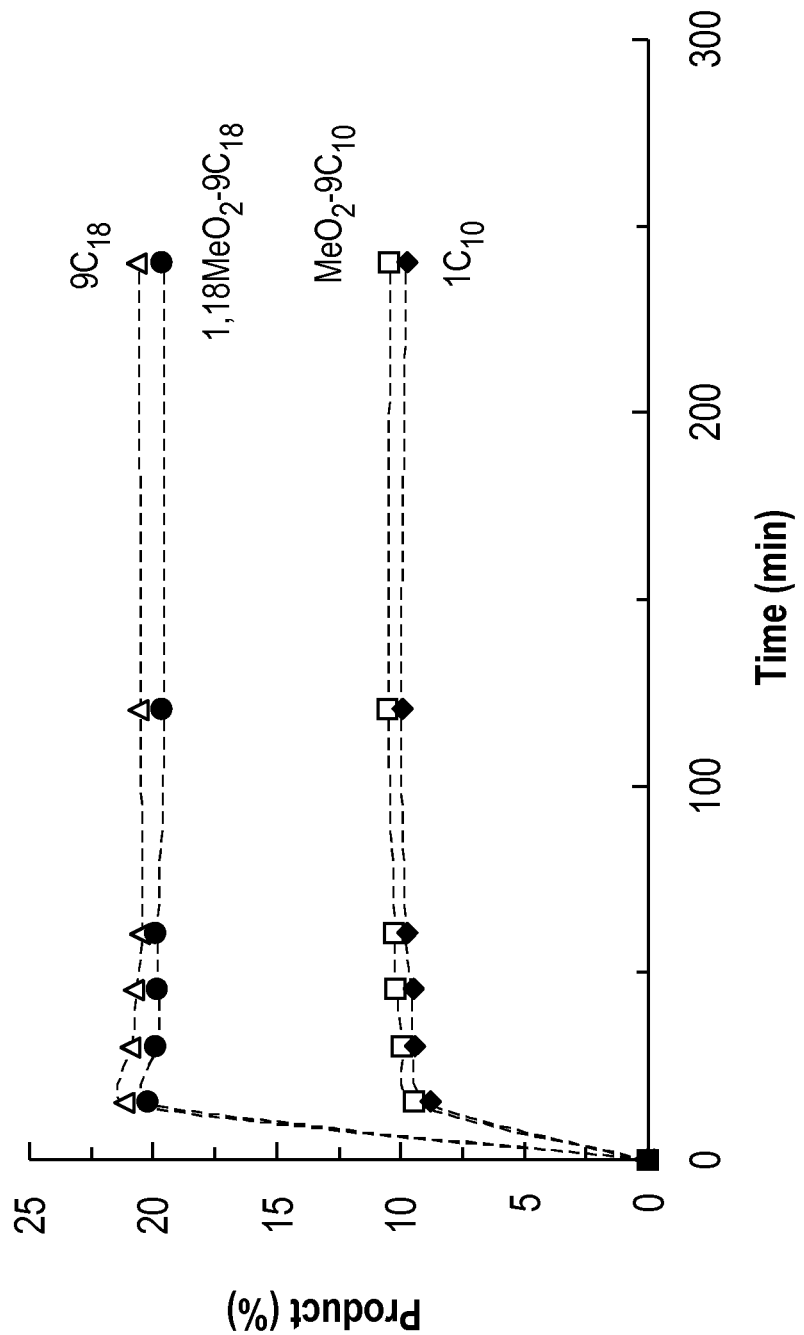

SYNTHESIS OF TERMINAL ALKENES FROM INTERNAL ALKENES AND ETHYLENE VIA OLEFIN METATHESIS

RELATED APPLICATIONS

This application is a continuation of U.S. patent application Ser. No. 13/913,814, filed Jun. 10, 2013, which is a continuing application of U.S. patent application Ser. No. 13/234,542, filed Sep. 16, 2011 (now U.S. Pat. No. 8,481,747, issued on Jul. 9, 2013), which is a divisional of U.S. patent application Ser. No. 11/879,029, filed Jul. 13, 2007 (now U.S. Pat. No. 8,067,610, issued on Nov. 29, 2011), which claims priority to U.S. Provisional App. No. 60/830,944, filed Jul. 13, 2006, the disclosures of which are incorporated herein by reference.

GOVERNMENT RIGHTS

This invention was made with Government support under grant no. DE-FG36-04GO14016 awarded by the Department of Energy. The U.S. Government has certain rights in this invention.

TECHNICAL FIELD

This invention relates generally to olefin metathesis, and more particularly relates to the synthesis of terminal alkenes from internal alkenes using a cross-metathesis reaction catalyzed by a selected olefin metathesis catalyst. The invention has utility in the fields of catalysis, organic synthesis, and industrial chemistry.

BACKGROUND

Ethenolysis is a specific cross metathesis reaction between an internal olefin and ethylene to produce terminal olefins. Scheme 1 demonstrates the ethenolysis reaction:

SCHEME 1

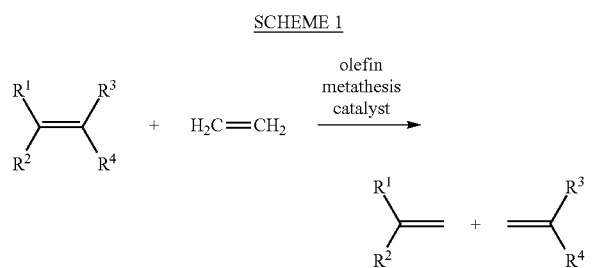

Examples of ethenolysis include the conversion of a mixture of ethylene and 2-butene into propene (as in the Phillips triolefin process and the Meta-4 process developed by the Institut Français du Pétrole), and the conversion of a mixture of ethylene and 2,4,4-trimethyl-2-pentene into neohexene. These processes typically use heterogeneous ill-defined olefin metathesis catalysts based on tungsten and rhenium oxides and which are not compatible with air, water, oxygenates, and many functional groups. The ethenolysis reaction has also been implemented in the conversion of seed oil-derived substrates such as fatty acid methyl esters (FAME) into terminally unsaturated carboxylic acids (e.g., 9-decenoic acid) and terminal olefins (e.g., 1-decene). The ethenolysis of FAME was originally performed with a heterogeneous, ill-defined rhenium catalyst to give turnover numbers (TON) of about 100. The so-called "first generation" Grubbs catalysts such as $Cl_2(PCy_3)_2Ru=CH-CH=CPh_2$, $Cl_2(PCy_3)_2Ru=CHPh$ ("C823"), and complexes that contain bicyclic phosphines, as well as first generation Grubbs-Hoveyda catalyst ("$C_{601}$"), have been used in the ethenolysis of vegetable oil-derived materials. The production of 1-octene from linoleic acid using an enzyme-mediated isomerization reaction, followed by a metathesis reaction using ethylene and various metathesis catalysts, has also been described. However, the conjugation present in these reactants necessitated a high catalyst loading and often resulted in a relatively low yield of terminal olefin products.

It is therefore desirable to provide a convenient and effective route for the production of terminal olefins. Compared with known metathesis methods, an ideal process would: substantially reduce the amount of catalyst that is needed for the cross-metathesis reaction; provide a high degree of selectivity for the preparation of terminal olefins from internal olefins; and allow the use of a mixture of internal olefins from a variety of sources. An ideal process would also not require isomerization of the olefinic substrate prior to the metathesis reaction, and an ideal process would allow for the preparation of terminal olefins directly from seed oils and from the component materials of seed oils, or from non-isomerized derivatives of seed oils.

SUMMARY OF THE DISCLOSURE

Accordingly, the disclosure is directed to addressing one or more of the aforementioned issues, and, in one embodiment, provides a method for synthesizing a terminal olefin. The method comprises contacting an olefinic substrate comprised of at least one internal olefin with ethylene in the presence of a metathesis catalyst. The catalyst is present in an amount that is less than about 1000 ppm relative to the olefinic substrate. The metathesis catalyst has the structure of formula (II)

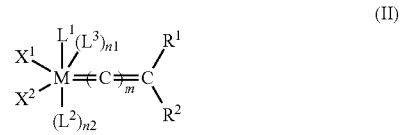

wherein:
m is zero, 1, or 2;
M is Ru or Os;
n1 and n2 are independently selected from zero and 1;
$X^1$ and $X^2$ are anionic ligands, and may be the same or different;
$R^1$ and $R^2$ are independently selected from H, hydrocarbyl, substituted hydrocarbyl, heteroatom-containing hydrocarbyl, and substituted heteroatom-containing hydrocarbyl;
$L^2$ and $L^3$ are neutral electron donating ligands, and may be the same or different; and
$L^1$ is a carbene ligand with the structure of formula (IIIa)

wherein:
$Z^1$ is $-N(Ar^1)(R^9)$ and $Z^2$ is $-N(Ar^2)(R^{9A})$ or $-C(R^{10})(R^{11})(R^{12})$;

$Ar^1$ and $Ar^2$ are independently aryl substituted with at least one group selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl; and $R^9$, $R^{9A}$, $R^{10}$, $R^{11}$, and $R^{12}$ are independently selected from hydrogen, hydrocarbyl, substituted hydrocarbyl, heteroatom-containing hydrocarbyl, and substituted heteroatom-containing hydrocarbyl, provided that any two of $X^1$, $X^2$, $L^1$, $L^2$, $L^3$, $R^1$, $R^2$, $R^9$, $R^{9A}$, $R^{10}$, $R^{11}$, and $R^{12}$ may be taken together to form a cycle.

In another embodiment, the invention provides a method for synthesizing a terminal olefin. The method comprises contacting, under reaction conditions effective to prepare a terminal olefin, an olefinic substrate comprising a mixture of mono-, di-, and tri-glycerides with ethylene in the presence of a ruthenium alkylidene metathesis catalyst. The catalyst comprises an N-heterocyclic carbene ligand, and the olefinic substrate comprises at least one internal olefin.

In yet another embodiment, the invention provides a method for synthesizing a terminal olefin. The method comprises contacting, under reaction conditions effective to prepare a terminal olefin, an olefinic substrate with ethylene in the presence of a ruthenium alkylidene metathesis catalyst. The olefinic substrate comprises at least one internal olefin, and further comprises a seed oil or a composition derived from a seed oil. The catalyst comprises an N-heterocyclic carbene ligand. At least about 50% of the metathesis reaction products comprise a terminal olefin and at least about 50% of the internal olefins initially present in the reaction mixture are converted into terminal olefins.

In a still further embodiment, the invention provides a method for synthesizing a terminal olefin. The method comprises contacting, in the presence of a metathesis catalyst, an olefinic substrate comprising at least one internal olefin with ethylene. The metathesis catalyst has the structure of formula (IIA)

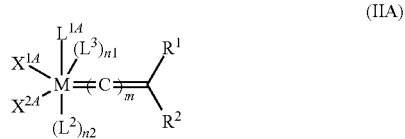

(IIA)

wherein:

m is 0, 1, or 2;

M is Ru or Os;

n1 and n2 are independently selected from zero and 1;

$X^{1A}$ and $X^{2A}$ are $CF_3CO_2$;

$R^1$ and $R^2$ are independently selected from H, hydrocarbyl, substituted hydrocarbyl, heteroatom-containing hydrocarbyl, and substituted heteroatom-containing hydrocarbyl;

$L^2$ and $L^3$ are neutral electron donating ligands; and $L^{1A}$ is an N-heterocyclic carbene ligand.

In a still further embodiment, the invention provides a method for synthesizing a terminal olefin. The method comprises contacting, under reaction conditions effective to prepare a terminal olefin, an olefinic substrate with ethylene, in the presence of a metathesis catalyst. The olefinic substrate comprises at least one internal olefin, and comprises a seed oil or a composition derived from a seed oil. The metathesis catalyst comprises an N-heterocyclic carbene ligand and is present in an amount that is less than about 50 ppm.

BRIEF DESCRIPTION OF THE DRAWINGS

FIG. 1 is a graph showing the results from an etheneolysis reaction of methyl oleate and ethylene.

DETAILED DESCRIPTION OF THE INVENTION

Terminology and Definitions: Unless otherwise indicated, the invention is not limited to specific reactants, substituents, catalysts, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefin, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively. If not otherwise indicated, the terms "alkyl" and "lower alkyl" include primary, secondary, and tertiary alkyl and lower alkyl.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$, $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$), phospho (—PO$_2$), phosphino (—PH$_2$), silyl (—SiR$_3$ wherein R is hydrogen or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Methods and Compositions:

Accordingly, the invention provides an olefin cross-metathesis method for synthesizing a terminal olefin from ethylene and an olefinic substrate comprised of at least one internal olefin. The reactions are carried out catalytically, in the presence of a ruthenium alkylidene metathesis catalyst.

In a first embodiment of the invention, then, the olefin metathesis reaction is carried out by contacting the at least one internal olefin with ethylene in the presence of the metathesis catalyst under reaction conditions effective to allow cross-metathesis to occur.

The olefin metathesis catalyst for carrying out the cross-metathesis reactions of the invention is preferably a Group 8 transition metal complex having the structure of formula (II)

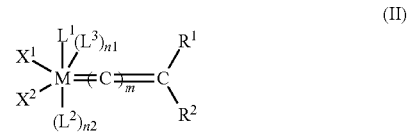

wherein:
m is zero, 1, or 2;
M is Ru or Os;
n1 and n2 are independently selected from zero and 1;
$X^1$ and $X^2$ are anionic ligands and may be the same or different;
$R^1$ and $R^2$ are independently selected from H, hydrocarbyl, substituted hydrocarbyl, heteroatom-containing hydrocarbyl, and substituted heteroatom-containing hydrocarbyl;
$L^2$ and $L^3$ are neutral electron donating ligands and may be the same or different; and
$L^1$ is a carbene ligand with the structure of formula (IIIa)

wherein:
$Z^1$ is —N(Ar$^1$)(R$^9$) and $Z^2$ is —N(Ar$^2$)(R$^{9A}$) or —C(R$^{10}$)(R$^{11}$)(R$^{12}$);
Ar$^1$ and Ar$^2$ are independently aryl substituted with at least one group selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl; and
$R^9$, $R^{9A}$, $R^{10}$, $R^{11}$, and $R^{12}$ are independently selected from hydrogen, hydrocarbyl, substituted hydrocarbyl, heteroatom-containing hydrocarbyl, and substituted heteroatom-containing hydrocarbyl,
wherein any two of $X^1$, $X^2$, $L^1$, $L^2$, $L^3$, $R^1$, $R^2$, $R^9$, $R^{9A}$, $R^{10}$, $R^{11}$, and $R^{12}$ may be taken together to form a cycle.

Preferred catalysts contain Ru or Os as the Group 8 transition metal, with Ru particularly preferred.

Numerous embodiments of the catalysts useful in the reactions of the invention are described in more detail infra. For the sake of convenience, the catalysts are described in groups, but it should be emphasized that these groups are not meant to be limiting in any way. That is, any of the catalysts useful in the invention may fit the description of more than one of the groups described herein.

A first group of catalysts having the structure of formula (II) is commonly referred to as Second Generation Grubbs-type catalysts. For catalysts of the first group, M, n1, n2, and m are as described above, and $X^1$, $X^2$, $L^1$, $L^2$, $L^3$, $R^1$, and $R^2$ are further described as follows.

$L^2$ is selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —C≡C(CH$_3$)$_2$.

Any two or more (typically two, three, or four) of $X^1$, $X^2$, $L^1$, $L^2$, $L^3$, $R^1$, and $R^2$ can be taken together to form a cyclic group. When any of $X^1$, $X^2$, $L^1$, $L^2$, $L^3$, $R^1$ and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

$L^1$ is a carbene ligand with the structure of formula (IIIa)

(IIIa)

wherein $Z^1$ is —N(Ar$^1$)(R$^9$) and $Z^2$ is —N(Ar$^2$)(R$^{9A}$) or —C(R$^{10}$)(R$^{11}$)(R$^{12}$). Ar$^1$ and Ar$^2$ are aryl substituted with at least one group selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl, and Ar$^1$ and Ar$^2$ may be the same or different. $R^9$, $R^{9A}$, $R^{10}$, $R^{11}$, and $R^{12}$ are independently selected from hydrogen, hydrocarbyl, substituted hydrocarbyl, heteroatom-containing hydrocarbyl, and substituted heteroatom-containing hydrocarbyl. Furthermore, any two of $X^1$, $X^2$, $L^1$, $L^2$, $L^3$, $R^1$, $R^2$, $R^9$, $R^{9A}$, $R^{10}$, $R^{11}$, and $R^{12}$ may be taken together to form a cycle.

For example, $Z^1$ is —N(Ar$^1$)(R$^9$), $Z^2$ is —C(R$^{10}$)(R$^{11}$)(R$^{12}$), and $R^9$ and $R^{12}$ are linked. The linkage formed by $R^9$ and $R^{12}$ has the structure

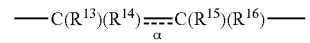

such that $L^1$ has the structure of formula (IIIb)

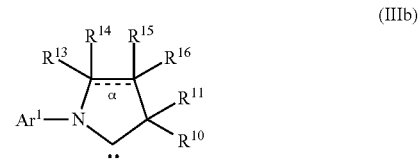

(IIIb)

wherein α is an optional double bond, and $R^{13}$, $R^{14}$, $R^{15}$, and $R^{16}$ are independently selected from hydrogen, hydrocarbyl, substituted hydrocarbyl, heteroatom-containing hydrocarbyl, and substituted heteroatom-containing hydrocarbyl, provided that $R^{14}$ and $R^{16}$ are not present if α is present, and provided that any two or more of Ar$^1$, $R^{10}$, $R^{11}$, $R^{13}$, $R^{14}$, $R^{15}$, and $R^{16}$ may be taken together to form a cyclic group. For example, $R^{10}$ and $R^{11}$ are taken together to form a cyclic group, such as a six-membered cyclic group.

In a preferred embodiment, Ar$^1$ has the structure of formula (VIIa)

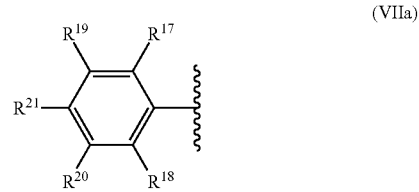

(VIIa)

wherein ∿ represents the attachment point to N in formula (IIIb), $R^{17}$ and $R^{18}$ are independently selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl, and $R^{19}$, $R^{20}$, and $R^{21}$ are independently selected from H, $C_1$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl. For example, $R^{19}$, $R^{20}$, and $R^{21}$ are H such that Ar$^1$ has the structure of formula (VIIb)

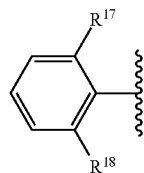

(VIIb)

wherein the wavy line represents the attachment point to N in formula (IIIb) and $R^{17}$ and $R^{18}$ are independently selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl. In a more preferred embodiment, $R^{17}$ and $R^{18}$ are independently $C_2$-$C_{12}$ alkyl; for example, $R^{17}$ and $R^{18}$ are both ethyl.

As another example, $Z^1$ is —N(Ar$^1$)(R$^9$) and $Z^2$ is —N(Ar$^2$)(R$^{9A}$). In a preferred embodiment, $R^9$ and $R^{9A}$ are linked such that $L^1$ has the structure of formula (IIIc)

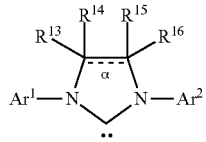

(IIIc)

wherein α is an optional double bond, Ar$^2$ is aryl substituted with at least one group selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl, and $R^{13}$, $R^{14}$, $R^{15}$, and $R^{16}$ are as described previously. In a preferred embodiment, $L^1$ has the formula of (IIId)

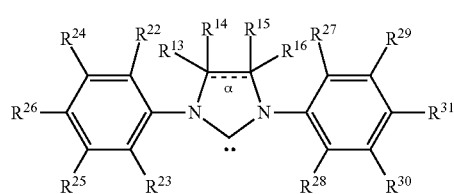

(IIId)

wherein $R^{22}$, $R^{23}$, $R^{27}$ and $R^{28}$ are independently selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl, and $R^{24}$, $R^{25}$, $R^{26}$, $R^{29}$, $R^{30}$, and $R^{31}$ are independently selected from H, $C_1$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl. For example, α is not present, and $L^1$ has the structure of formula (IIId-1)

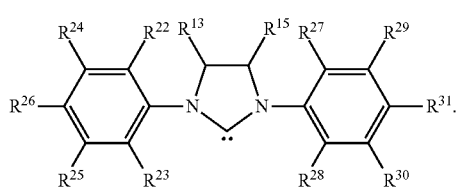

(IIId-1)

As a further example, α is not present, and $R^{13}$, $R^{14}$, $R^{15}$, $R^{16}$, $R^{24}$, $R^{25}$, $R^{26}$, $R^{29}$, $R^{30}$, and $R^{31}$ are each H such that $L^1$ has the structure of formula (IIIe)

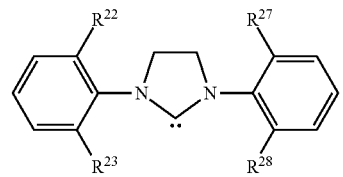

(IIIe)

wherein $R^{22}$, $R^{23}$, $R^{27}$, and $R^{28}$ are independently selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl. As a further example, $R^{22}$, $R^{23}$, $R^{27}$, and $R^{28}$ are each independently $C_3$-$C_{12}$ secondary alky or $C_4$-$C_{12}$ tertiary alkyl, and as a still further example, $R^{22}$, $R^{23}$, $R^{27}$, and $R^{28}$ are isopropyl.

Examples of N-heterocyclic carbene ligands suitable as $L^1$ also include the following:

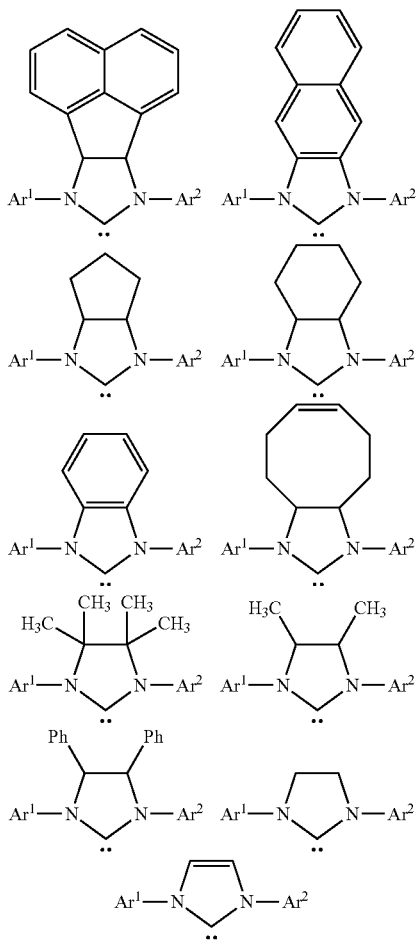

In a second group of catalysts having the structure of formula (II), M, m, n, $X^1$, $X^2$, $L^1$, R', and $R^2$ are as defined for the first group of catalysts having the structure of formula (II), and $L^2$ and $L^3$ are weakly coordinating neutral electron donor ligands in the form of optionally substituted heterocyclic groups. Again, n is zero or 1, such that $L^3$ may or may not be present. Generally, in the second group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

Examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_6$-$C_{24}$ aryl)-substituted carbamoyl, mono-($C_6$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_6$-$C_{24}$ aryl)-substituted amino, di-($C_5$-$C_{24}$ aryl)-substituted amino, di-N—($C_1$-$C_{20}$ alkyl), N—($C_6$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroalkaryl, $C_1$-$C_{12}$ alkoxy, $C_5$-$C_{14}$ aryloxy, $C_{12}$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_{1-5}$—$C_{1-14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VIII)

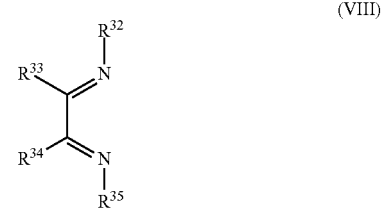

wherein $R^{32}$, $R^{33}$, $R^{34}$, and $R^{35}$ are independently hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{32}$ and $R^{33}$, (2) $R^{34}$ and $R^{35}$, (3) $R^{33}$ and $R^{34}$, or (4) both $R^{32}$ and $R^{33}$, and $R^{34}$ and $R^{35}$, may be taken together to form a ring, i.e., an N-heterocycle. Preferred cyclic groups in such a case are five- and six-membered rings, typically aromatic rings.

A third group of catalysts having the structure of formula (II), includes catalysts wherein M, n1, n2, m, $X^1$, $X^2$, $R^1$, $R^2$, $L^1$, $L^2$, and $L^3$ are as defined for any of the previously defined catalysts, and two of the substituents are taken together to form a bidentate ligand or a tridentate ligand.

Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

For example, m is zero, and $L^2$ and $R^2$ are taken together to form a cycle. Catalysts of this type are commonly called "Grubbs-Hoveyda" catalysts, and have the structure of formula (IIa)

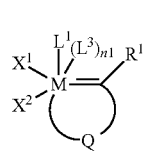

(IIa)

wherein Q is selected from hydrocarbylene, substituted hydrocarbylene, heteroatom-containing hydrocarbylene, and substituted heteroatom-containing hydrocarbylene, wherein two or more substituents on adjacent atoms within Q may also be taken together to form an additional, optionally substituted cyclic structure. For example, Grubbs-Hoveyda catalysts may have the structure of formula (IIb)

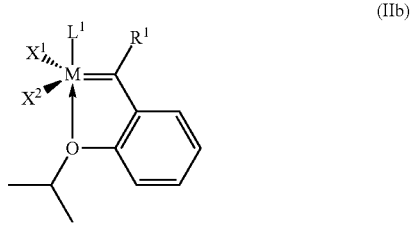

(IIb)

Further examples of Grubbs-Hoveyda-type catalysts include the following:

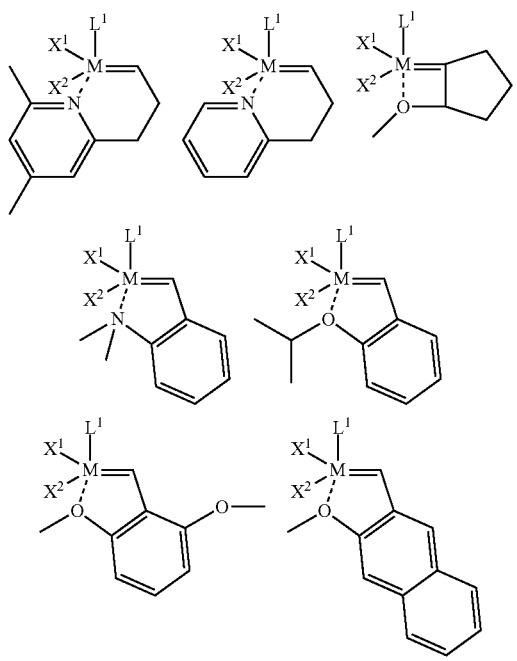

wherein $L^1$, $X^1$, $X^2$, and M are as described for any of the other groups of catalysts.

In addition to the catalysts that have the structure of formula (II), as described above, other transition metal carbene complexes may be used in the reactions disclosed herein, including:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexacoordinated, and are of the general formula (X)

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14, are penta-coordinated, and are of the general formula (XII)

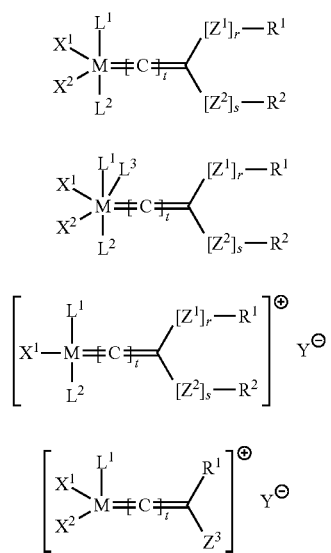

(IX)

(X)

(XI)

(XII)

wherein: $X^1$, $X^2$, $L^1$, $L^2$, n, $L^3$, $R^1$ and $R^2$ are as defined for any of the previously defined four groups of catalysts; r and s are independently zero or 1; t is an integer in the range of zero to 5; Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ is any cationic moiety such as —P$(R^2)_3$, or —N$(R^2)_3$; and any two or more of $X^1$, $X^2$, $L^1$, $L^2$, $L^3$, n, $Z^1$, $Z^2$, $Z^3$, R', and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, R', and $R^2$ may be attached to a support.

As is understood in the field of catalysis, suitable solid supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

Non-limiting examples of catalysts that may be used in the reactions of the invention include the following, which for convenience are identified throughout this disclosure by reference to their molecular weight:

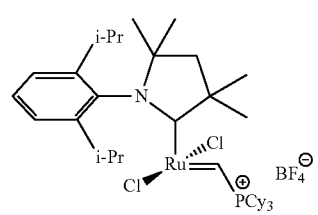

C838

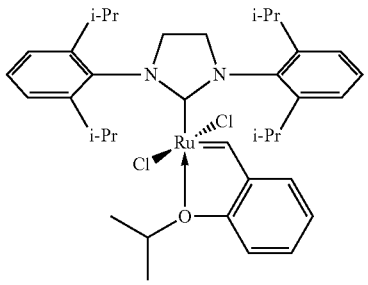

C712

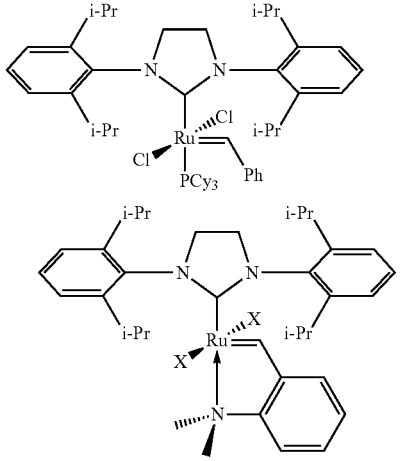

C933

C697 (X = Cl)
C785 (X = Br)
C879 (X = I)

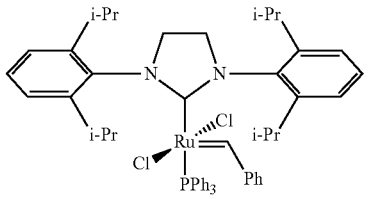

C916

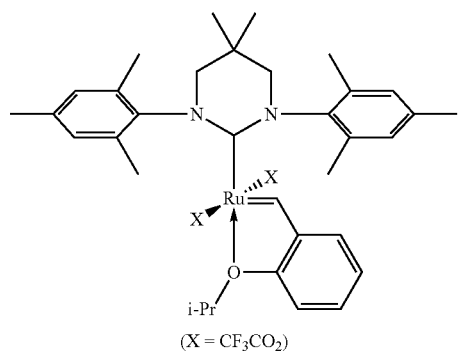

C824

(X = CF$_3$CO$_2$)

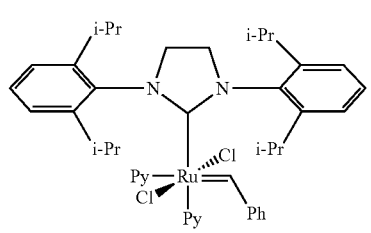

C811

-continued

C965-p

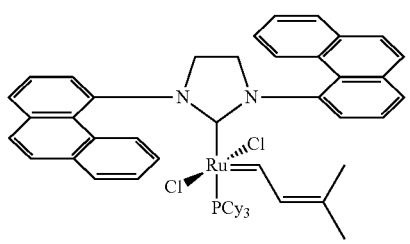

C646

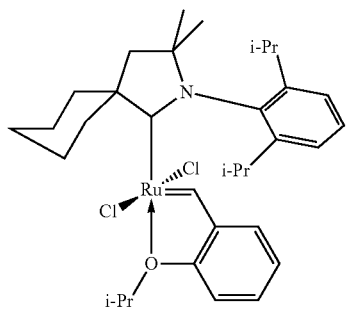

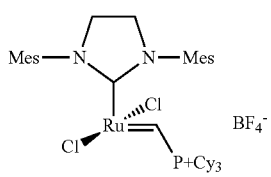

C767-m

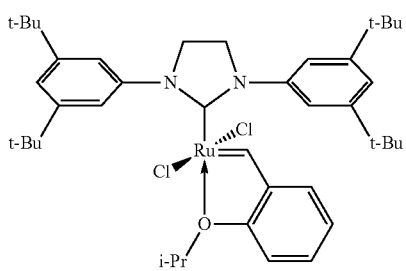

C606

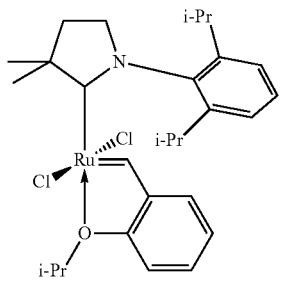

C578

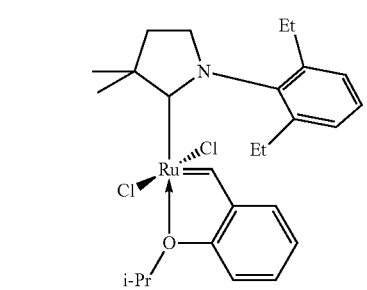

-continued

C577

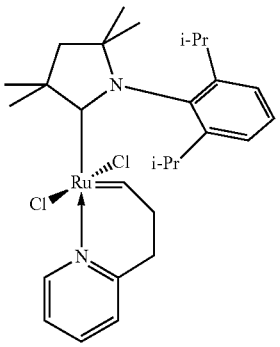

In the foregoing molecular structures and formulae, Ph represents phenyl, Cy represents cyclohexyl, i-Pr represents isopropyl, Et represents ethyl, t-Bu represents tertiary butyl, and py represents pyridine (coordinated through the N atom).

Further examples of catalysts useful in the reactions of the invention include the following: ruthenium (II) [1,3-bis-(2,4, 6-trimethylphenyl)-2-imidazolidinylidene]dichloro (phenylmethylene) (triphenylphosphine) (C830); ruthenium (II) dichloro (tricyclohexylphosphine) (o-isopropoxyphenylmethylene) ($C_{601}$), and ruthenium (II) (1,3-bis-(2,4,6,-trimethylphenyl)-2-imidazolidinylidene)dichloro (phenylmethylene) (bis 3-bromopyridine (C884)).

The transition metal complexes used as catalysts herein can be prepared by several different methods, such as those described by Schwab et al. (1996) J. Am. Chem. Soc. 118: 100-110, Scholl et al. (1999) Org. Lett. 6:953-956, Sanford et al. (2001) J. Am. Chem. Soc. 123:749-750, U.S. Pat. No. 5,312,940 and U.S. Pat. No. 5,342,909. Also see U.S. Patent Publication No. 2003/0055262 to Grubbs et al. filed Apr. 16, 2002 for "Group 8 Transition Metal Carbene Complexes as Enantioselective Olefin Metathesis Catalysts", International Patent Publication No. WO 02/079208 application Ser. No. 10/115,581 to Grubbs, Morgan, Benitez, and Louie, filed Apr. 2, 2002, for "One-Pot Synthesis of Group 8 Transition Metal Carbene Complexes Useful as Olefin Metathesis Catalysts," commonly assigned herewith to the California Institute of Technology. Preferred synthetic methods are described in International Patent Publication No. WO 03/11455A1 to Grubbs et al. for "Hexacoordinated Ruthenium or Osmium Metal Carbene Metathesis Catalysts," published Feb. 13, 2003.

Reactants:

The olefinic substrate comprises at least one internal olefin, and may have 2 or more internal olefins. For example, the olefinic substrate may comprise in the range of 2 to about 15, 2 to about 10, or 2 to about 5 internal olefins. By "internal olefin" is meant an olefin wherein each of the olefinic carbons is substituted by at least one non-hydrogen substituent. The non-hydrogen substituents are selected from hydrocarbyl, substituted hydrocarbyl, heteroatom-containing hydrocarbyl, substituted heteroatom-containing hydrocarbyl, and functional groups. The internal olefin is therefore at least disubstituted, and may further include additional non-hydrogen substituents such that the internal olefin is tri- or tetra-substituted. Each of the substituents on the internal olefinic carbons may be further substituted as described supra. The internal olefin may be in the Z- or E-configuration. When the olefinic substrate comprises a plurality of internal olefins, the olefinic substrate may comprise a mixture of internal olefins (varying

C859 in stereochemistry and/or substituent identity), or may comprise a plurality of identical internal olefins.

The olefinic substrate may be a single compound or a mixture of compounds. The olefinic substrate may be hydrophobic or hydrophilic, although in a preferred embodiment, the olefinic substrate is hydrophobic.

For example, the olefinic substrate may be represented by the formula $(R^I)(R^{II})C$═$C(R^{III})(R^{IV})$, wherein $R^I$, $R^{II}$, $R^{III}$, and $R^{IV}$ are independently selected from H, hydrocarbyl, substituted hydrocarbyl, heteroatom-containing hydrocarbyl, substituted heteroatom-containing hydrocarbyl, and functional groups, provided that at least one of $R^I$ or $R^{II}$ and at least one of $R^{III}$ or $R^{IV}$ is other than H. In a preferred embodiment, either $R^I$ or $R^{II}$ and either $R^{III}$ or $R^{IV}$ is H, such that the internal olefin is disubstituted.

As another example, the olefinic substrate is an ester of glycerol (a "glyceride"), and has the structure of formula (I)

wherein $R_I$, $R^{VI}$, and $R^{VII}$ are independently selected from hydrogen, hydrocarbyl, substituted hydrocarbyl, heteroatom-containing hydrocarbyl, substituted heteroatom-containing hydrocarbyl, and functional groups, provided that at least one of $R^V$, $R^{VI}$, and $R^{VII}$ is other than hydrogen and comprises an internal olefin. In a preferred embodiment, the olefinic substrate comprises glycerol esterified with 1, 2, or 3 fatty acids, such that the olefinic substrate is a monoacylglycerol, diacylglycerol, or triacylglycerol (i.e., a monoglyceride, diglyceride, or triglyceride, respectively), or a mixture thereof. Each fatty acid-derived fragment of the olefinic substrate may independently be saturated, monounsaturated, or polyunsaturated, and may furthermore derive (or be derivable) from naturally-occurring fatty acids or from synthetic fatty acids. For example, the olefinic substrate may comprise glycerol esterified with one, two, or three fatty acids that are independently selected from $CH_3(CH_2)_n COOH$, where n is 2, 3, 4, 5, 6, 7, 8, 9, 10, 11, 12, 13, 14, 15, 16, 17, 18, 19, 20, 21, or 22, palmitoleic acid, vaccenic acid, erucic acid, oleic acid, alpha-linolenic acid, gamma-linolenic acid, linoleic acid, gadoleic acid, arachidonic acid, docosahexaenoic acid (i.e., DHA), eicosapentaenoic acid (i.e., EPA), and $CH_3$—$R^{VIII}$—$COOH$, where $R^{VIII}$ is substituted or unsubstituted $C_2$-$C_{24}$ alkenylene. The olefinic substrate may be solid (e.g., a fat) or liquid (e.g., an oil).

Preferred olefinic substrates are seed oils, or are compounds that derive from seed oils.

The olefinic substrate may be a compound or mixture of compounds that is derived from a seed oil or glyceride using any one or combination of methods well known in the chemical arts. Such methods include saponification, esterification, hydrogenation, isomerization, oxidation, and reduction. For example, the olefinic substrate may the carboxylic acid or mixture of carboxylic acids that result from the saponification of a monoacylglycerol, diacylglycerol, triacylglycerol, or mixture thereof. In a preferred embodiment, the olefinic substrate is a fatty acid methyl ester (FAME), i.e., the methyl ester of a carboxylic acid that is derived from a glyceride. Sunflower FAME, safflower FAME, soy FAME (i.e., methyl soyate), and canola FAME are examples of such olefinic substrates. In addition, preferred olefinic substrates include seed oil-derived compounds such as methyl oleate.

Sources of unsaturated esters of glycerol include synthesized oils, natural oils (e.g., seed oils, vegetable oils), animal fats, similar sources and any combinations thereof. Representative examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, combinations of these, and the like. Representative examples of animal fats include lard, tallow, chicken fat, yellow grease, fish oil, combinations of these, and the like. A representative example of a synthesized oil includes tall oil, which is a byproduct of wood pulp manufacture.

The at least one internal olefin is reacted with ethylene, a cross-metathesis partner, in the cross-metathesis reactions of the invention. Ethylene may be provided in the form of a condensed liquid, but in a preferred embodiment, ethylene is provided in the form of a gas. Typically, the pressure of a gaseous cross-metathesis partner over the reaction solution is maintained in a range that has a minimum of about 10 psi, 50 psi, or 80 psi, and a maximum of about 100 psi, 150 psi, 180 psi, 200 psi, 500 psi, 800 psi, or 1000 psi.

Procedures and Reaction Conditions

The components of the reactions of the invention may be combined in any order, and it will be appreciated that the order of combining the reactants may be adjusted as needed. For example, the catalyst may be added to the olefinic substrate, followed by addition of ethylene. As another example, a flask containing the olefinic substrate may be pressurized with ethylene, followed by addition of the catalyst (as, for example, a concentrated solution in a solvent as described herein). The catalyst may be added to the reaction either as a solid or dissolved in a solvent. The catalyst might be added in any quantities and manner effective for the intended results of the reaction. For example in applications where minimization of catalyst's bimolecular decomposition is desired, predetermined amounts of catalyst can be sequentially added to the reaction mixture at predetermined time intervals.

The reactions of the invention may be carried out in a solvent, and any solvent that is inert towards cross-metathesis may be employed. Generally, solvents that may be used in the cross-metathesis reactions include organic, protic, or aqueous solvents, such as aromatic hydrocarbons, chlorinated hydrocarbons, ethers, aliphatic hydrocarbons, alcohols, water, or mixtures thereof. Example solvents include benzene, toluene, p-xylene, methylene chloride, 1,2-dichloroethane, dichlorobenzene, chlorobenzene, tetrahydrofuran, diethylether, pentane, methanol, ethanol, water, or mixtures thereof. In a preferred embodiment, the reactions of the invention are carried out neat, i.e., without the use of a solvent.

It will be appreciated that the temperature at which a cross-metathesis reaction according to the invention is conducted can be adjusted as needed, and may be at least about −78° C., −40° C., −10° C., 0° C., 10° C., 20° C., 25° C., 40° C., 60° C., 100° C., or 150° C. In a preferred embodiment, the reactions are carried out at a temperature of at least about 40° C., and in another preferred embodiment, the reactions are carried out at a temperature of at least about 60° C.

The reactions of the invention are catalyzed by any of the metathesis catalysts that are described supra. The catalyst is typically added to the reaction medium as a solid, but may also be added as a solution wherein the catalyst is dissolved in an appropriate solvent. It will be appreciated that the amount of catalyst that is used (i.e., the "catalyst loading") in the reaction is dependent upon a variety of factors such as the identity of the reactants (including the identity of the catalyst), and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, 1000 ppm, or 10,000 ppm relative to the amount of the olefinic substrate. Catalyst loading, when measured in ppm relative to the amount of the olefinic substrate, is calculated using the equation $$ppm \text{ catalyst} = \frac{\text{moles catalyst}}{\text{moles olefinic substrate}} * 1{,}000{,}000.$$

Alternatively, the amount of catalyst can be measured in terms of mol % relative to the amount of olefinic substrate, using the equation $$\text{mol \% catalyst} = \frac{\text{moles catalyst}}{\text{moles olefinic substrate}} * 100.$$

Thus, the catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, 0.1 mol %, or 1 mol % relative to the olefinic substrate. In a second embodiment of the invention, the olefin metathesis reaction is carried out by contacting, in the presence of a ruthenium alkylidene metathesis catalyst, an olefinic substrate comprised of a mixture of monoglycerides, diglycerides, and triglycerides, with ethylene, under reaction conditions effective to allow cross-metathesis to occur. The olefinic substrate comprises at least one internal olefin, and the metathesis catalyst has the structure of formula (II)

$$(II)$$

wherein:

m is zero, 1, or 2;

M is Ru or Os;

n1 and n2 are independently selected from zero and 1;

$X^1$ and $X^2$ are anionic ligands;

$R^1$ and $R^2$ are independently selected from H, hydrocarbyl, substituted hydrocarbyl, heteroatom-containing hydrocarbyl, and substituted heteroatom-containing hydrocarbyl;

$L^2$ and $L^3$ are neutral electron donating ligands; and $L^1$ is a carbene ligand with the structure of formula (IIIa)

$$(IIIa)$$

wherein:

$Z^1$ is —N(Ar$^1$)(R$^9$) and $Z^2$ is —N(Ar$^2$)(R$^{9A}$) or —C(R$^{10}$)(R$^{11}$)(R$^{12}$);

Ar$^1$ and Ar$^2$ are independently aryl substituted with at least one group selected from $C_2$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl; and $R^9$, $R^{9A}$, $R^{10}$, $R^{11}$, and $R^{12}$ are independently selected from hydrogen, hydrocarbyl, substituted hydrocarbyl, heteroatom-containing hydrocarbyl, and substituted heteroatom-containing hydrocarbyl, wherein any two of $X^1$, $X^2$, $L^1$, $L^2$, $L^3$, $R^1$, $R^2$, $R^9$, $R^{9A}$, $R^{10}$, $R^{11}$, and $R^{12}$ may be taken together to form a cycle.

The disclosure for the first embodiment of the invention (e.g., reactants and reaction conditions described supra) also applies for this embodiment.

In a third embodiment of the invention, the olefin metathesis reaction comprises contacting, under reaction conditions effective to prepare a terminal olefin, an olefinic substrate comprising a seed oil or a composition derived from a seed oil and further comprising at least one internal olefin with ethylene in the presence of a ruthenium alkylidene metathesis catalyst comprising an N-heterocyclic carbene ligand, wherein at least about 50% of the metathesis reaction products comprise a terminal olefin and further wherein at least about 50% of the internal olefins initially present in the reaction mixture are converted into terminal olefins. The disclosure for the first embodiment of the invention (e.g., reactants and reaction conditions described supra) also applies for this embodiment.

In a fourth embodiment of the invention, the olefin metathesis reactions comprise contacting, in the presence of a metathesis catalyst, an olefinic substrate comprising at least one internal olefin with ethylene, wherein the metathesis catalyst has the structure of formula (IIA)

$$(IIA)$$

wherein:

m is 0, 1, or 2;

n1 and n2 are independently selected from zero and 1;

$X^{1A}$ and $X^{2A}$ are $CF_3CO_2$;

$R^1$ and $R^2$ are independently selected from H, hydrocarbyl, substituted hydrocarbyl, heteroatom-containing hydrocarbyl, and substituted heteroatom-containing hydrocarbyl;

$L^2$ and $L^3$ are neutral electron donating ligands; and $L^{1A}$ is an N-heterocyclic carbene ligand.

The disclosure for the first embodiment of the invention (e.g., reactants and reaction conditions described supra) also applies for this embodiment.

In a fifth embodiment of the invention, the olefin metathesis reactions comprise contacting, under reaction conditions effective to prepare a terminal olefin, an olefinic substrate comprising a seed oil or a composition derived from a seed oil and further comprising at least one internal olefin with ethylene, in the presence of a metathesis catalyst, wherein the metathesis catalyst comprises an N-heterocyclic carbene ligand and is present in an amount that is less than about 50 ppm. The disclosure for the first embodiment of the invention (e.g., reactants and reaction conditions described supra) also applies for this embodiment.

It is to be understood that while the invention has been described in conjunction with the preferred specific embodiments thereof, that the description above as well as the examples that follow are intended to illustrate and not limit the scope of the invention. Other aspects, advantages, and modifications within the scope of the invention will be apparent to those skilled in the art to which the invention pertains.

EXAMPLES

General Procedures

Low Pressure (<200 Psi) Ethenolyses:

Ethenolyses of research grade methyl oleate were set up under an inert atmosphere in a glove box. As an example reaction procedure, a Fisher-Porter bottle equipped with a stir bar was charged with methyl oleate (>99%) from Nu-Check-Prep (Elysian, Minn.) (15.0 g; 50.6 mmol). A solution of olefin metathesis catalyst of an appropriate concentration was prepared in anhydrous dichloromethane (from Aldrich) and the desired volume of this solution added to the methyl oleate. The head of the Fisher-Porter bottle was equipped with a pressure gauge and a dip-tube was adapted on the bottle. The system was sealed and taken out of the glove box to an ethylene line. The vessel was then purged 3 times with ethylene (Polymer purity 99.9% from Matheson Tri Gas), pressurized to the indicated pressure and placed in an oil bath at the indicated temperature. The reaction was monitored by collecting samples into vials at different reaction times via the dip-tube. Immediately after collecting a sample, the reaction was stopped by adding 1 mL of a 1.0 M isopropanol solution of tris-hydroxymethylphopshine (THMP) to the vial. The samples were then heated for at least 1 hour at 60° C., diluted with 1 mL of distilled water, extracted with 1 mL of hexanes and analyzed by gas chromatography (GC).

High Pressure (>200 Psi) Ethenolyses:

High pressure ethenolyses of research grade methyl were run according to a procedure analogous to that for low pressure ethenolyses, except that a high-pressure stainless steel reactor (Parr) was used in place of the Fisher-Porter bottles.

GC Analytical Method:

The GC analyses were run using a flame ionization detector (FID). The following conditions and equipment were used:

Column: Rtx-5, 30m×0.25 mm (ID)×0.25 μm film thickness.
Manufacturer: Restek
GC and column conditions: Injector temperature: 250° C.
Detector temperature: 280° C.
Oven temperature: Starting temperature: 100° C., hold time: 1 minute.
Ramp rate 10° C./min to 250° C., hold time: 12 minutes.
Carrier gas: Helium
Mean gas velocity: 31.3±3.5% cm/sec (calculated)
Split ratio: ~50:1

Example 1

Ethenolysis of Mo

Ethenolysis reactions using various first and second generation Grubbs catalysts were run according to the general procedure. Data are provided in Table 1.

TABLE 1

Comparison of first and second generation catalysts in ethenolysis of MO.[a]

| Entry | Catalyst | Temp (° C.) | Time (min) | Conversion (%)[b] | Selectivity (%)[c] | Yield (%)[d] | TON[e] | TOF (min$^{-1}$)[f] |
|---|---|---|---|---|---|---|---|---|
| 1 | C823 | 40 | 120 | 58 | 93 | 54 | 5,400 | 45 |
| 2 | C823 | 60 | 30 | 54 | 89 | 48 | 4,800 | 160 |
| 3 | C601 | 40 | 30 | 51 | 94 | 48 | 4,800 | 160 |
| 4 | C848 | 40 | 120 | 64 | 44 | 28 | 2,800 | 23 |
| 5 | C848 | 60 | <15 | 64 | 44 | 28 | 2,800 | >190 |
| 6 | C627 | 40 | 30 | 60 | 33 | 20 | 2,000 | 67 |
| 7 | C627 | 60 | <15 | 68 | 47 | 32 | 3,200 | >210 |

[a]General conditions: neat MO, 150 psi ethylene, catalyst loading = 100 ppm
[b]Conversion = 100 − [(final moles of MO)*100/(initial moles of MO)]
[c]Selectivity = (moles of ethenolysis products)*100/(moles of total products)
[d]Yield = (moles of ethenolysis products)*100/(initial moles of MO) = Conversion*Selectivity/100
[e]TON = Yield*[(moles of MO)/(moles of Cat.)]
[f]TOF = TON/Time Example 2

Ethenolysis of MO

Ethenolysis reactions using various catalysts were run according to the general procedure. Data are provided in Table 2.

TABLE 2

Comparison of various catalysts in the ethenolysis of MO

| Entry | Cat. | Loading (ppm) | Time (min) | Conversion (%) | Selectivity (%) | Yield (%) | TON | TOF (min$^{-1}$) |
|---|---|---|---|---|---|---|---|---|
| 1[a] | C848 | 100 | 120 | 64 | 44 | 28 | 2,800 | 23 |
| 2[b] | C848 | 100 | <15 | 64 | 44 | 28 | 2,800 | >190 |
| 3[a] | C627 | 100 | 30 | 60 | 33 | 20 | 2,000 | 67 |
| 4[b] | C627 | 100 | <15 | 68 | 47 | 32 | 3,200 | >210 |
| 5[a] | C782 | 100 | <15 | 38 | 71 | 27 | 2,700 | >180 |
| 6[b] | C782 | 100 | <15 | 53 | 60 | 32 | 3,200 | >210 |

TABLE 2-continued

Comparison of various catalysts in the ethenolysis of MO

| Entry | Cat. | Loading (ppm) | Time (min) | Conversion (%) | Selectivity (%) | Yield (%) | TON | TOF (min$^{-1}$) |
|---|---|---|---|---|---|---|---|---|
| 7[a] | C712 | 100 | 30 | 70 | 56 | 39 | 3,900 | 130 |
| 8[b] | C712 | 100 | <15 | 79 | 71 | 56 | 5,600 | >373 |
| 9[a] | C712 | 35 | <15 | 69 | 57 | 39 | 11,000 | >733 |
| 10[c] | C712 | 100 | 360 | 87 | 80 | 70 | 7,000 | 19 |
| 11[c] | C712 | 25 | 360 | 51 | 63 | 32 | 12,800 | 36 |
| 12[a] | C933 | 100 | 60 | 69 | 55 | 38 | 3,800 | 63 |
| 13[a] | C933 | 10 | 60 | 61 | 36 | 22 | 22,000 | 367 |
| 14[a] | C866 | 100 | 30 | 49 | 94 | 46 | 4,600 | 150 |
| 15[b] | C866 | 100 | <15 | 43 | 88 | 38 | 3,800 | >250 |
| 16[c] | C866 | 100 | <30 | 39 | 92 | 36 | 3,600 | >120 |
| 17[c] | C866 | 500 | <15 | 86 | 94 | 81 | 1,620 | >110 |
| 18[d] | C697 | 100 | 1260 | 66 | 53 | 35 | 3,560 | <3 |
| 19[e] | C697 | 100 | 390 | 79 | 72 | 57 | 5,710 | 15 |
| 20[f] | C697 | 100 | 120 | 81 | 67 | 54 | 5,410 | 45 |
| 21[a] | C785 | 100 | 1380 | 58 | 55 | 32 | 3,200 | <3 |
| 22[b] | C785 | 100 | 180 | 78 | 73 | 57 | 5,640 | 31 |
| 23[b] | C859 | 100 | 240 | 77 | 66 | 51 | 5,200 | 22 |
| 24[g] | C859 | 100 | 30 | 76 | 61 | 46 | 4,680 | 156 |
| 25[a] | C859 | 100 | 1200 | 71 | 59 | 42 | 4,200 | <4 |
| 26[a] | C879 | 100 | 390 | 51 | 69 | 35 | 3,570 | 9 |
| 27[b] | C879 | 100 | 240 | 59 | 90 | 53 | 5,370 | 22 |
| 28[b] | C965-p | 100 | 30 | 58 | 45 | 26 | 2,500 | 84 |
| 29[b] | C824 | 100 | 30 | 35 | 86 | 30 | 2,990 | 100 |
| 30[a] | C606 | 100 | 1,320 | 61 | 92 | 56 | 5,600 | 4 |
| 31[a] | C606 | 50 | 1,200 | 61 | 93 | 57 | 11,400 | 10 |
| 32[a] | C578 | 100 | <30 | 73 | 73 | 53 | 5,300 | >177 |
| 33[a] | C578 | 35 | 60 | 75 | 75 | 56 | 16,000 | 267 |
| 34[a] | C578 | 10 | <30 | 42 | 83 | 35 | 35,000 | >1,167 |
| 35[a] | C646 | 100 | 360 | 46 | 94 | 43 | 4,200 | 12 |
| 36[a] | C838 | 100 | 1320 | 60 | 90 | 54 | 5,440 | 4 |
| 37[g] | C577 | 100 | 300 | 74 | 84 | 62 | 6,330 | 21 |
| 38[b] | C577 | 100 | 1380 | 67 | 90 | 60 | 6,150 | <5 |
| 39[a] | C767-m | 100 | 30 | 37 | 32 | 12 | 1,150 | 38 |
| 40[a] | C811 | 100 | 15 | 62 | 34 | 21 | 2,100 | 140 |
| 41[a] | C916 | 100 | 15 | 65 | 45 | 29 | 2,900 | 194 |
| 42[b] | C827 | 100 | 120 | 75 | 64 | 48 | 4,790 | 40 |

[a]neat MO; 40° C.; 150 psi ethylene.
[b]neat MO; 60° C.; 150 psi ethylene.
[c]neat MO; 25° C.; 800 psi ethylene.
[d]neat MO; 40° C.; 180 psi ethylene.
[e]neat MO; 60° C.; 180 psi ethylene.
[f]neat MO; 80° C.; 180 psi ethylene.
[g]neat MO; 80° C.; 150 psi ethylene Example 3

Ethenolysis of MO

Ethenolysis reactions using various catalysts were run according to the general procedure. Data are provided in Table 3.

TABLE 3

Comparison of C606 and C578 to C848 and C627 in ethenolysis of MO[a]

| Entry | Cat. | Loading (ppm) | Time (min) | Conversion (%) | Selectivity (%) | Yield (%) | TON | TOF (min$^{-1}$) |
|---|---|---|---|---|---|---|---|---|
| 1 | C848 | 100 | 120 | 64 | 44 | 28 | 2,800 | 23 |
| 2 | C627 | 100 | 30 | 60 | 33 | 20 | 2,000 | 67 |
| 3 | C606 | 100 | 1,320 | 61 | 92 | 56 | 5,600 | 4 |
| 4 | C606 | 50 | 1,200 | 61 | 93 | 57 | 11,400 | 10 |
| 5 | C578 | 100 | <30 | 73 | 73 | 53 | 5,300 | >177 |
| 6 | C578 | 35 | 60 | 75 | 75 | 56 | 16,000 | 267 |
| 7 | C578 | 10 | <30 | 42 | 83 | 35 | 35,000 | >1,167 |

[a]Conditions: neat MO; 40° C.; 150 psi ethylene.

Example 4

Ethenolysis of Pure Methyl Oleate with 2"" Generation Catalysts

As in the reaction shown below, methyl oleate was reacted with ethylene and 100 ppm of catalyst $C_{627}$ according to the general procedure given above. The results are illustrated in the graph shown in FIG. 1.

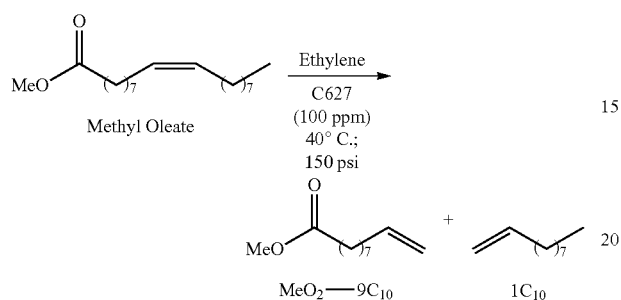

What is claimed is:

1. A method for synthesizing a metathesis reaction product having a terminal olefin, the method comprising contacting, in the presence of a metathesis catalyst, an olefinic substrate comprised of at least one internal olefin with ethylene, wherein the catalyst is present in an amount that is less than about 1000 ppm relative to the amount of the olefinic substrate, and wherein the metathesis catalyst has the structure of formula (XII):

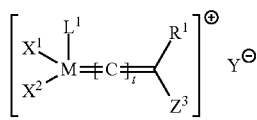

(XII)

wherein:
M is Ru or Os;
t is zero;
$X^1$ and $X^2$ are anionic ligands;
$R^1$ and $R^2$ are independently selected from the group consisting of hydrogen, hydrocarbyl, substituted hydrocarbyl, heteroatom-containing hydrocarbyl, and substituted heteroatom-containing hydrocarbyl;
$Z^3$ is a cationic moiety selected from the group consisting of $P(R^2)_3$ and $N(R^2)_3$;
Y is a non-coordinating anion; and
$L^1$ is a carbene ligand with the structure of formula (IIIc):

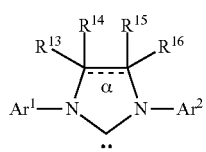

(IIIc)

wherein $Ar^1$ and $Ar^2$ are independently aryl substituted with at least one group selected from the group consisting of $C_1$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl; a is an optional double bond; $R^{13}$, $R^{14}$, $R^{15}$, and $R^{16}$ are independently selected from the group consisting of hydrogen, hydrocarbyl, substituted hydrocarbyl, heteroatom-containing hydrocarbyl, and substituted heteroatom-containing hydrocarbyl, wherein any two or more of $A^1$, $Ar^2$, $R^{13}$, $R^{14}$, $R^{15}$, and $R^{16}$ may be taken together to form a cyclic group, and provided that $R^{14}$ and $R^{16}$ are not present if a is present.

2. The method of claim 1, wherein $L^1$ has the structure of formula (IIId):

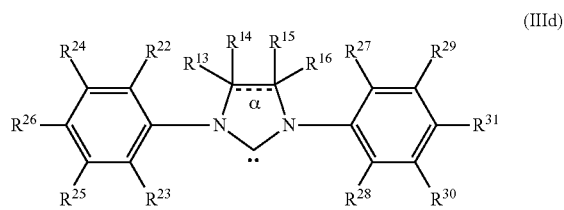

(IIId)

wherein $R^{22}$, $R^{23}$, $R^{27}$, and $R^{28}$ are independently selected from the group consisting of $C_1$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl, and $R^{24}$, $R^{25}$, $R^{26}$, $R^{29}$, $R^{30}$, and $R^{31}$ are independently selected from hydrogen, $C_1$-$C_{12}$ alkyl, $C_2$-$C_{12}$ alkenyl, $C_2$-$C_{12}$ alkynyl, $C_5$-$C_{12}$ aryl, $C_6$-$C_{12}$ aralkyl, and $C_6$-$C_{12}$ alkaryl.

3. The method of claim 2, wherein a is not present, such that $L^1$ has the structure of formula (IIId-1):

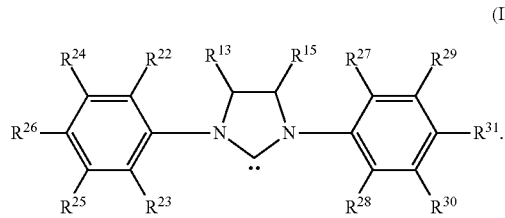

(IIId-1)

4. The method of claim 3, wherein $R^{24}$, $R^{25}$, $R^{26}$, $R^{29}$, $R^{30}$, and $R^{31}$ are hydrogen, such that $L^1$ has the structure of formula (IIIe):

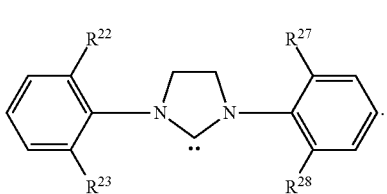

(IIIe)

5. The method of claim 1, wherein the catalyst is:

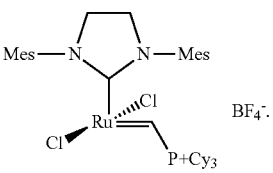

6. The method of claim 1, wherein the catalyst is present in an amount that is 100 ppm or less relative to the amount of the olefinic substrate.

7. The method of claim 1, wherein the olefinic substrate is selected from the group consisting of seed oils, alkyl esters of unsaturated fatty acids, and aryl esters of unsaturated fatty acids.

8. The method of claim 1, wherein the olefinic substrate comprises a mixture of internal olefins selected from the group consisting of monoacylglycerols, diacylglycerols, triacylglycerols, and combinations thereof.

9. The method of claim 1, wherein the olefinic substrate is of the formula $(R^{I})(R^{II})C=C(R^{III})(R^{IV})$, wherein $R^{I}$, $R^{II}$, $R^{III}$, and $R^{IV}$ are independently selected from the group consisting of hydrogen, hydrocarbyl, substituted hydrocarbyl, heteroatom-containing hydrocarbyl, substituted heteroatom-containing hydrocarbyl, and functional groups, provided that at least one of $R^{I}$ or $R^{II}$ and at least one of $R^{III}$ or $R^{IV}$ is other than hydrogen.

\* \* \* \* \*